(12) United States Patent
Moriya et al.

(10) Patent No.: US 7,105,299 B2
(45) Date of Patent: Sep. 12, 2006

(54) METHOD FOR DETERMINING CHUM SALMON HAPLOTYPE USING MITOCHONDRIAL DNA

(75) Inventors: Shogo Moriya, Chiba (JP); Tatsuo Ichihara, Chiba (JP); Osamu Suzuki, Chiba (JP); Akihisa Urano, Sapporo (JP); Syuiti Abe, Sapproro (JP)

(73) Assignee: Nisshinbo Industries, Inc., Tokyo (JP)

( * ) Notice: Subject to any disclaimer, the term of this patent is extended or adjusted under 35 U.S.C. 154(b) by 537 days.

(21) Appl. No.: 10/317,449

(22) Filed: Dec. 12, 2002

(65) Prior Publication Data

US 2003/0124608 A1     Jul. 3, 2003

(30) Foreign Application Priority Data

Dec. 13, 2001 (JP) .............................. 2001-379926

(51) Int. Cl.
C12Q 1/68 (2006.01)
C07H 21/02 (2006.01)
C07H 21/04 (2006.01)

(52) U.S. Cl. ................... 435/6; 536/23.1; 536/24.3
(58) Field of Classification Search .................... 435/6; 536/23.1, 24.3
See application file for complete search history.

(56) References Cited

U.S. PATENT DOCUMENTS

| | | | | |
|---|---|---|---|---|
| 5,837,832 A * | 11/1998 | Chee et al. | ................ | 536/22.1 |
| 6,458,583 B1 * | 10/2002 | Bruhn et al. | ............. | 435/287.2 |
| 2003/0082588 A1 * | 5/2003 | Garimella | ...................... | 435/6 |
| 2003/0198952 A9 * | 10/2003 | Okamoto et al. | ............. | 453/6 |

OTHER PUBLICATIONS

Seeb et al., Transactions of the American Fisheries Society 128(1): 88-103 (1999).*
Scribner et al., Canadian Journal of Fisheries and Aquatic Sciences 55 (7): 1748-1758 (Jul. 1998).*
Cronin et al., Canadian Journal of Fisheries and Aquatic Sciences 50 (4): 708-715 (1993).*
Orum et al., Clinical Chemistry 44 (11): 1898-1905 (1999).*
Landegren et al., A ligase mediated gene detection technique. Science 241 : 1077-1080 (1988).*
Sato, et al. "Genetic Variation Among Japanese Populations of Chum Salmon Inferred from the Nucleotide Sequences of the Mitochondrial DNA Control Region." *Zoological Science*, 18: 99-106 (2001).
Guo, et al. "Direct Fluorescence Analysis of Genetic Polymorphisms by Hybridization with Oligonucleotide Arrays on Glass Supports," *Nucleic Acids Research*, vol. 22, No. 24, pp. 5456-5465, 1994.

Park, et al. Low Levels of Intraspeciofic Variation in the Mitochondrial DNA of Chum Salmon (*Oncorhynchus keta*), *Molecular Marine Biology and Biotechnology*, vol. 2, No. 6, pp. 362-370, 1993.
Sato, et al. Database accession No. AB039897, abstract XP002234157, Oct. 3, 2000.
Sato, et al. Database accession No. AB039895, abstract XP002234158, Oct. 3, 2000.
Sato, et al. Database accession No. AB039900, abstract XP002234159, Oct. 3, 2000.
Sato, et al. Database accession No. AB039901, abstract XP002234160, Oct. 3, 2000.
Sato, et al. Database accession No. AB039899, abstract XP002234161, Oct. 3, 2000.
Sato, et al. Database accession No. AB039898, abstract XP002234163, Oct. 3, 2000.
Sato, et al. Database accession No. AB039893, abstract XP002234164, Oct. 3, 2000.
Sato, et al. Database accession No. AB039891, abstract XP002234165, Oct. 3, 2000.
Sato, et al. Database accession No. AB039890, abstract XP002234166, Oct. 3, 2000.
Sato, et al. Database accession No. AB039894, abstract XP002234167, Oct. 3, 2000.
Sato, et al. Database accession No. AB039896, abstract XP002234162, Oct. 3, 2000.
Sato, et al. "Genetic Differentiation Among Pacific Rim Chum Salmon Populations Inferred from the Nucleotide Sequence Variation of the Mitochondrial DNA Control Region," 71st Annual Meeting of the Zoological Society of Japan, *Zoological Science*, Supplement, vol. 17, p. 24, 2000.
European Search Report, issued in a related foreign case, Mar. 10, 2003.

* cited by examiner

*Primary Examiner*—Ethan Whisenant
(74) *Attorney, Agent, or Firm*—Knobbe, Martens, Olson & Bear, LLP

(57) ABSTRACT

A kit comprising an oligonucleotide-immobilized substrate obtained by immobilizing, on a substrate, one or more kinds of oligonucleotides that enable detection of a polymorphism in a nucleotide sequence of mitochondrial DNA control region of chum salmon, of which standard is represented by the nucleotide sequence of SEQ ID NO: 8, at a position selected from the 10th, 30th, 42nd, 57th, 70th, 96th, 108th, 154th, 194th, 231st, 242nd, 250th, 260th, 339th, 340th, 386th, 395th, 401st and 471st positions is used to detect the polymorphism based on hybridization of the oligonucleotides with a nucleic acid derived from specimen chum salmon and thereby determine a haplotype of the specimen chum salmon.

13 Claims, 3 Drawing Sheets

Fig. 2

METHOD FOR DETERMINING CHUM SALMON HAPLOTYPE USING MITOCHONDRIAL DNA

RELATED APPLICATIONS

This application claims priority of Japanese Application No. 2001-379926, filed Dec. 13, 2001 which is incorporated herein by reference in its entirety.

FIELD OF THE INVENTION

The present invention relates to a method and kit for determining a chum salmon haplotype. More specifically, the present invention relates to a method for determining a chum salmon haplotype by using mitochondrial DNA.

DESCRIPTION OF THE RELATED ART

Chum salmon (*Oncorhynchus keta*) is known as an anadromous fish homing to the mother (natal) river. Examples of methods for identifying subpopulations of chum salmon distributed in the sea include capture and recapture experiments, allozyme analysis and polymorphic analysis of mitochondrial DNA.

As for the capture and recapture experiments, information about distribution of chum salmon has been obtained by offshore liberation. However, most of those recaptured are adult fish, which homes to their mother (natal) river for spawning within the year, and information about distribution of young fish or immature fish in the sea can hardly be obtained. Moreover, since places for the capture and recapture experiments are limited and recapture efforts vary depending on the regions, the composition of a subpopulation cannot be even estimated.

In the allozyme analysis, methods for scoring alleles on loci of allozyme polymorphic genes have been unified for chum salmon, and baseline data has been established. The composition of a subpopulation of a mixed group can be estimated by comparing this baseline data and the observed gene frequency of salmon mixed offshore. However, this method suffers from problems that skills are required for the handling of tissues, that many specimens cannot be treated, and so forth.

Nucleotide mutations are concentrated in the control region of mitochondrial DNA of chum salmon. Investigation of the mitochondrial DNA control regions of chum salmon collected from several rivers in Japan revealed that the chum salmon could be classified into several haplotypes (small-scale genotypes)(Zoological Science, 18, 99–106). In this report, distribution of the haplotypes in Japan could be obtained. However, in order to identify subpopulations of chum salmon distributed in the sea, polymorphic information about all the regions where chum salmon are distributed needs to be obtained.

Further, as a method for examining polymorphism in mitochondrial DNA, there can be mentioned a method for determining nucleotide sequences by using a DNA sequencer. In this method, however, sequences must be read several times for one specimen in order to prevent reading errors of the sequences. Further, since distribution of haplotypes in a chum salmon population is required to be investigated, many specimens must be treated at one time, but it is difficult to deal many specimens by using a DNA sequencer.

SUMMARY OF THE INVENTION

An object of the present invention is to provide a method and kit for determining a chum salmon haplotype based on polymorphism in mitochondrial DNA, which are suitable for dealing many specimens and allow highly precise typing of one specimen by one test.

The inventors of the present invention assiduously studied in order to achieve the aforementioned objects. As a result, they found that, in classification of haplotypes of chum salmon based on polymorphisms that existed in nucleotide sequences of the first half on the 5' side of the mitochondrial DNA control region of chum salmon, biased distribution of haplotypes in the chum salmon population correlated to regions to which the fish homed, and that a haplotype of a test specimen could be determined in high precision by hybridization using immobilized oligonucleotides that could detect the aforementioned polymorphisms, and thus accomplished the present invention.

That is, the present invention provides the followings.

(1) A kit for determining a haplotype of specimen chum salmon, which comprises an oligonucleotide-immobilized substrate obtained by immobilizing, on a substrate, one or more kinds of oligonucleotides that enable detection of a polymorphism in a nucleotide sequence of mitochondrial DNA control region of chum salmon, of which standard is represented by the nucleotide sequence of SEQ ID NO: 8, at a position selected from the 10th, 30th, 42nd, 57th, 70th, 96th, 108th, 154th, 194th, 231st, 242nd, 250th, 260th, 339th, 340th, 386th, 395th, 401st and 471st positions by hybridization, and with which the haplotype is determined based on a polymorphism or a combination of polymorphisms detected by hybridization of the oligonucleotides with a nucleic acid derived from the specimen chum salmon.

(2) The kit according to (1), wherein the polymorphism or combination of polymorphisms is selected from the following polymorphism or polymorphisms:
(1) 96D
(2) 96D, T10C
(3) 96D, A42G
(4) 96D, A108C
(5) 96D, A194T
(6) 96D, T231C
(7) 96D, A471C
(8) No polymorphism
(9) 96D, 386D, C395A
(10) 96D, 386D, C395A, C154G
(11) 96D, 386D, C395A, T231C
(12) 96D, 386D, C395A, C154G, T10C
(13) 96D, 386D, C395A, C154G, T70C
(14) 96D, 386D, C395A, C154G, A108C
(15) 96D, 386D, C395A, C154G, T231C
(16) 96D, 386D, C395A, C154G, C242T
(17) 96D, 386D, C395A, C154G, T250C
(18) 96D, 386D, C395A, C154G, A260G
(19) 96D, 386D, C395A, C154G, T339A
(20) 96D, 386D, C395A, C154G, T401C
(21) 96D, 386D, C395A, C154G, A471C
(22) 96D, 386D, C395A, C154G, T339A, C340T
(23) 96D, 386D, C395A, C154G, T339A, T401C
(24) 96D, T30C
(25) 96D, T30C, A57T
(26) 96D, T30C, T70C
(27) 96D, T30C, A108A
(28) 96D, T30C, T231C (the numbers represent positions in SEQ ID NO: 8, characters on the right and left of each number represent substitution of the right nucleotide for the left nucleotide, and D represents deletion).

(3) The kit according to (2), wherein the one or more polymorphisms include at least one or more polymorphisms selected from (2), (3), (4), (12), (13), (14), (15), (16), (17), (18), (19), (20), (21), (22), (23) and (26).

(4) The kit according to any one of (1) to (3), wherein each oligonucleotide has a nucleotide sequence complementary or homologous to a nucleotide sequence of a region including a polymorphic site and has a length of 10 to 40 nucleotides.

(5) The kit according to any one of (1) to (4), wherein a reference oligonucleotide, which includes the polymorphic site and has a nucleotide sequence complementary or homologous to a nucleotide sequence that does not exhibit a polymorphism and a length of 10 to 40 nucleotides, is further immobilized.

(6) The kit according to any one of (1) to (5), wherein each oligonucleotide is immobilized on the substrate, of which surface is coated with carbodiimide groups or isocyanate groups, through a reaction between a carbodiimide group or isocyanate group and a linker added to an end of the oligonucleotide.

(7) The kit according to (6), wherein the linker is an amino group or a compound that has an amino group or a homopolymer of thymidine residues at an end thereof.

(8) The kit according to (6) or (7), wherein each oligonucleotide is immobilized on a site having a size of 10 μm to 5 cm in diameter of the surface of the substrate.

(9) The kit according to any one of (1) to (8), wherein each oligonucleotide is DNA, RNA, peptide nucleic acid or locked nucleic acid.

(10) The kit according to any one of (1) to (9), wherein at least one of the oligonucleotides is an oligonucleotide of which binding affinity in hybridization is reduced by substitution of a spacer compound for an arbitrary nucleotide unrelated to a gene polymorphism.

(11) The kit according to (10), wherein the spacer compound is a nucleic acid structure that does not have complementary binding property to any kind of nucleotides.

(12) The kit according to any one of (1) to (11), wherein a region to which the specimen chum salmon homing area is estimated based on the haplotype of the specimen chum salmon.

(13) The kit according to any one of (1) to (12), wherein each oligonucleotide is selected from the nucleotide sequences of SEQ ID NOS: 29 to 64 or oligonucleotides having a nucleotide sequence obtained by extending or shortening any of these nucleotide sequences on the 5' or 3' side or the both sides.

(14) An oligonucleotide which enables detection of any of the following polymorphisms in a nucleotide sequence of mitochondrial DNA control region of chum salmon, of which standard is represented by the nucleotide sequence of SEQ ID NO: 8, by hybridization:
(2) 96D, T10C
(3) 96D, A42G
(4) 96D, A108C
(12) 96D, 386D, C395A, C154G, T10C

(13) 96D, 386D, C395A, C154G, T70C
(14) 96D, 386D, C395A, C154G, A108C
(15) 96D, 386D, C395A, C154G, T231C
(16) 96D, 386D, C395A, C154G, C242T
(17) 96D, 386D, C395A, C154G, T250C
(18) 96D, 386D, C395A, C154G, A260G
(19) 96D, 386D, C395A, C154G, T339A
(20) 96D, 386D, C395A, C154G, T401C
(21) 96D, 386D, C395A, C154G, A471C
(22) 96D, 386D, C395A, C154G, T339A, C340T
(23) 96D, 386D, C395A, C154G, T339A, T401C
(26) 96D, T30C, T70C (the numbers represent positions in SEQ ID NO: 8, characters on the right and left of each number represent substitution of the right nucleotide for the left nucleotide, and D represents deletion).

(15) A method for determining a haplotype of specimen chum salmon by hybridizing a nucleic acid derived from the specimen chum salmon with each oligonucleotide contained in the kit according to any one of (1) to (13), detecting presence or absence of formation of a hybrid of each oligonucleotide and the nucleic acid derived from the specimen chum salmon and identifying a polymorphism in the nucleotide sequence of the chum salmon mitochondrial DNA control region.

According to the present invention, a haplotype of chum salmon can be efficiently determined with high precision. Further, a region to which the chum salmon homes can be estimated according to the present invention.

BRIEF EXPLANATION OF THE DRAWINGS

FIG. 2 shows an example of preferred arrangement of capture oligonucleotides immobilized on a substrate.

Figure 1:
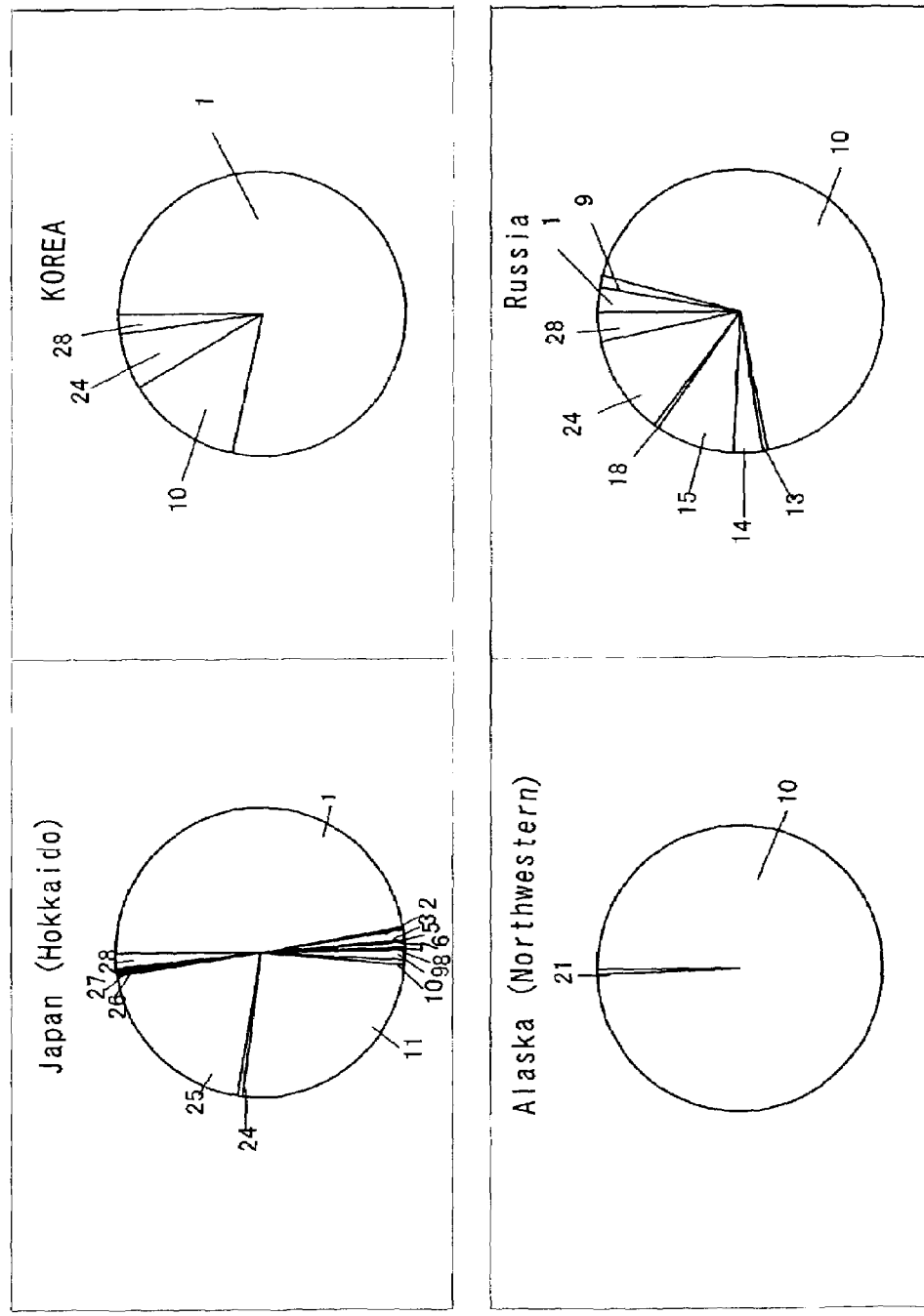
FIG. 1 shows 28 kinds of chum salmon haplotypes and their biased distribution of chum salmon homing area.

: Haplotypes matched in the method of the present invention and in the DNA sequencing method x: Haplotypes that are not matched in the method of the present invention and the DNA sequencing method

DETAILED DESCRIPTION OF THE PREFERRED EMBODIMENTS

The present invention will be explained in more detail hereafter.

The present invention provides a method and kit for determining a haplotype of specimen chum salmon by detecting a polymorphism existing in the mitochondrial DNA control region of the specimen chum salmon and identifying the polymorphism. As the polymorphism existing in the mitochondrial DNA control region, there can be mentioned polymorphisms existing in the first half of the control region on the 5' side, which corresponds to the nucleotide sequence of SEQ ID NO: 8. In the present invention, positions and types of the polymorphisms are represented by using the nucleotide sequence of SEQ ID NO: 8 as a standard.

Specific examples of the polymorphism include one or more polymorphisms at positions selected from the 10th, 30th, 42nd, 57th, 70th, 96th, 108th, 154th, 194th, 231st, 242nd, 250th, 260th, 339th, 340th, 386th, 395th, 401st and 471st positions in the nucleotide sequence of SEQ ID NO: 8. More specifically, there can be mentioned substitution of cytosine for thymine at the 10th position, substitution of cytosine for thymine at the 30th position, substitution of guanine for adenine at the 42nd position, substitution of thymine for adenine at the 57th position, substitution of cytosine for thymine at the 70th position, deletion of adenine at the 96th position, substitution of cytosine or thymine for adenine at the 108th position, substitution of guanine for cytosine at the 154th position, substitution of thymine for adenine at the 194th position, substitution of cytosine for thymine at the 231st position, substitution of thymine for cytosine at the 242nd position, substitution of cytosine for thymine at the 250th position, substitution of guanine for adenine at the 260th position, substitution of adenine for thymine at the 339th position, substitution of thymine for cytosine at the 340th position, deletion of a guanine residue at the 386th position, substitution of adenine for cytosine at the 395th position, substitution of cytosine for thymine at the 401st position and substitution of cytosine for adenine at the 471st position.

In the present invention, a haplotype is determined by identifying any of the aforementioned polymorphisms or combination(s) thereof. Table 1 shows 28 kinds of polymorphisms found in chum salmon. In the column of "Polymorphic site" in Table 1, positions in nucleotide sequence of SEQ ID NO: 8 as a standard are mentioned. Of these, Nos. 1, 5, 6, 7, 8, 9, 10, 11, 24, 25, 27 and 28 are known polymorphisms. The other polymorphisms are novel polymorphisms found by the inventors of the present invention. The nucleotide sequences of the mitochondrial DNA control regions of individual organisms are shown as SEQ ID NOS: 1 to 28. The sequence numbers correspond to the numbers of individuals.

When haplotypes of chum salmon that have homed to the native place are examined based on the aforementioned 28 kinds of haplotypes, deviation depending on the regions is observed. One example is shown in FIG. 1.

In the present invention, the polymorphisms are detected by using an oligonucleotide-immobilized substrate comprising a substrate on which one or more kinds of oligonucleotides are immobilized, which oligonucleotides enable detection of the polymorphisms by hybridization. Hereafter, these oligonucleotides may be referred to as capture oligonucleotides. Each capture oligonucleotide has a nucleotide sequence complementary or homologous to the nucleotide sequence of a region including a polymorphic site.

The capture oligonucleotide can be designed so as to include a polymorphic site specific to each haplotype existing in the control region. Further, upon designing a capture oligonucleotide, a type-specific nucleotide sequence of the capture oligonucleotide is preferably positioned in the central portion of the capture oligonucleotide. Further, one or more type-specific polymorphisms may exist in one capture oligonucleotide.

The length of the capture oligonucleotide is desirably 10 to 40 nucleotides. When it is shorter than that range, detection of hybridization may becomes difficult. When it is longer than that range, difference in hybridization with a type-specific sequence may be reduced, and determination of the type may become difficult. However, the length of the capture oligonucleotide primarily depends on characteristics of the sequence such as content of each nucleotide and repetition of the same nucleotide. Further, when there is a secondary structural failure, which is a factor of preventing hybridization, such a failure can also be avoided by using an

TABLE 1

| No. | 10 | 30 | 42 | 57 | 70 | 96 | 108 | 154 | 194 | 231 | 242 | 250 | 260 | 339 | 340 | 386 | 395 | 401 | 471 |
|---|---|---|---|---|---|---|---|---|---|---|---|---|---|---|---|---|---|---|---|
| 1 | T | T | A | A | T | — | A | C | A | T | C | T | A | T | C | G | C | T | A |
| 2 | C | T | A | A | T | — | A | C | A | T | C | T | A | T | C | G | C | T | A |
| 3 | T | T | G | A | T | — | A | C | A | T | C | T | A | T | C | G | C | T | A |
| 4 | T | T | A | A | T | — | C | C | A | T | C | T | A | T | C | G | C | T | A |
| 5 | T | T | A | A | T | — | A | C | T | T | C | T | A | T | C | G | C | T | A |
| 6 | T | T | A | A | T | — | A | C | A | C | C | T | A | T | C | G | C | T | A |
| 7 | T | T | A | A | T | — | A | C | A | T | C | T | A | T | C | G | C | T | C |
| 8 | T | T | A | A | T | A | A | C | A | T | C | T | A | T | C | G | C | T | A |
| 9 | T | T | A | A | T | — | A | C | A | T | C | T | A | T | C | — | A | T | A |
| 10 | T | T | A | A | T | — | A | G | A | T | C | T | A | T | C | — | A | T | A |
| 11 | T | T | A | A | T | — | A | C | A | C | C | T | A | T | C | — | A | T | A |
| 12 | C | T | A | A | T | — | A | G | A | T | C | T | A | T | C | — | A | T | A |
| 13 | T | T | A | A | C | — | A | G | A | T | C | T | A | T | C | — | A | T | A |
| 14 | T | T | A | A | T | — | C | G | A | T | C | T | A | T | C | — | A | T | A |
| 15 | T | T | A | A | T | — | A | G | A | C | C | T | A | T | C | — | A | T | A |
| 16 | T | T | A | A | T | — | A | G | A | T | T | T | A | T | C | — | A | T | A |
| 17 | T | T | A | A | T | — | A | G | A | T | C | C | A | T | C | — | A | T | A |
| 18 | T | T | A | A | T | — | A | G | A | T | C | T | G | T | C | — | A | T | A |
| 19 | T | T | A | A | T | — | A | G | A | T | C | T | A | A | C | — | A | T | A |
| 20 | T | T | A | A | T | — | A | G | A | T | C | T | A | T | C | — | A | C | A |
| 21 | T | T | A | A | T | — | A | G | A | T | C | T | A | T | C | — | A | T | C |
| 22 | T | T | A | A | T | — | A | G | A | T | C | T | A | A | T | — | A | T | A |
| 23 | T | T | A | A | T | — | A | G | A | T | C | T | A | A | C | — | A | C | A |
| 24 | T | C | A | A | T | — | A | C | A | T | C | T | A | T | C | G | C | T | A |
| 25 | T | C | A | T | T | — | A | C | A | T | C | T | A | T | C | G | C | T | A |
| 26 | T | C | A | A | C | — | A | C | A | T | C | T | A | T | C | G | C | T | A |
| 27 | T | C | A | A | T | — | T | C | A | T | C | T | A | T | C | G | C | T | A |
| 28 | T | C | A | A | T | — | A | C | A | C | C | T | A | T | C | G | C | T | A | oligonucleotide with reduced binding affinity in hybridization, which is reduced by substituting a spacer compound for an arbitrary nucleotide unrelated to a gene polymorphism. As such a spacer compound, a nucleic acid structure that does not have complementary binding property to any kind of nucleotides can be mentioned.

Exemplary nucleotide sequences of the capture oligonucleotide are shown as SEQ ID NOS: 29 to 64. In addition to the sequences shown as SEQ ID NOS: 29 to 64, there can be mentioned nucleotide sequences corresponding to any of the nucleotide sequences extended or shortened on the 5' or 3' side or the both sides so as to correspond to the nucleotide sequence of the mitochondrial DNA control region. However, the length of the capture oligonucleotide is preferably in the range of 10 to 40 nucleotides in any case.

The capture oligonucleotide may be any of DNA, RNA, peptide nucleic acid and locked nucleic acid. The capture oligonucleotide can be synthesized in the same manner as ordinary oligonucleotides by, for example, a method using a commercially available DNA synthesizer or the like.

In the present invention, the designed capture oligonucleotides well reflect the results of studies and researches before filing of the present application. However, if additional information is obtained thereafter about a nucleotide sequence of a novel haplotype, a novel capture oligonucleotide can be designed according to the method described in the present application, and such a capture oligonucleotide falls within the scope of the present invention.

The aforementioned capture oligonucleotide is immobilized on a substrate. Such a substrate is not particularly limited so long as it allows the capture oligonucleotide to be immobilized thereon and it can withstand during reaction processes required for hybridization with a test specimen and detection of a hybrid. Specific examples of the material for such a substrate include plastics, inorganic polymers, metals, natural polymers, ceramics and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, polyethylene fluoride, polyimide, acrylic resin and so forth.

Specific examples of the inorganic polymers include glass, quartz, carbon, silica gel, graphite and so forth.

Examples of the natural polymers include polyamino acids, cellulose, chitin, chitosan, alginic acid, derivatives thereof and so forth.

Specific examples of the ceramics include apatite, alumina, silica, silicon carbide, silicon nitride, boron carbide and so forth.

In the present invention, the shape of a substrate used for immobilization of the capture oligonucleotide is not particularly limited so long as the capture oligonucleotide can be immobilized thereon. Examples of the shape of such a substrate include plates, membranes, microparticles and so forth.

In the present invention, when a capture oligonucleotide is immobilized on the substrate, the capture oligonucleotide may be directly immobilized on the substrate, or the capture oligonucleotide may be immobilized on the substrate via a carrier carried on the substrate. As for the carrier, the carrier itself may have binding property to the capture oligonucleotide, or may immobilize the capture oligonucleotide via a ligand having binding property to the capture oligonucleotide. The term "carry" used herein means that the carrier is not substantially removed from the substrate in various solvents such as water-soluble solvents and organic solvents used when the capture oligonucleotide is immobilized on the carrier or the capture oligonucleotide-immobilized substrate is used in actual detection.

The aforementioned carrier used in the present invention may be carried by simply utilizing physical adhesion or may be chemically carried via a covalent bond or the like, so long as it is carried on the substrate. Further, the carrier may be carried on the whole surface of the substrate or may be carried on a part thereof as required.

Examples of the carrier include low molecular weight organic compounds, plastics, inorganic polymers, metals, natural polymers, ceramics and so forth.

Specific examples of the low molecular weight organic compounds include compounds containing a carbodiimide group, compounds containing an isocyanate group, compounds containing a nitrogen yperite group, compounds containing an aldehyde group, compounds containing an amino group and so forth.

Further, the same plastics, inorganic polymers, metals and ceramics as described above can be used.

Carriers particularly preferred in the present invention are compounds containing a carbodiimide group and compounds containing an isocyanate group.

The capture oligonucleotide is usually supplied to a substrate while it is contained in water or a buffer so that activity of the capture oligonucleotide should be maintained. Further, temperature at the time of supply is preferably 0 to 100° C. so that activity of the immobilized capture oligonucleotide should not be lost.

In the present invention, means for supplying the capture oligonucleotide, usually as water or buffer containing the nucleic acid, to the substrate is not particularly limited so long as the capture oligonucleotide is supplied while activity thereof is maintained. Examples of such means include a method using a dispenser, method using a pin, method using an ink jet and so forth.

When the capture oligonucleotide is immobilized on the substrate, shape of the site for the immobilization is not particularly limited so long as it does not affect hybridization or make detection difficult. Examples of the shape include circular shape, square shape and so forth. The size of the site of substrate on which each capture oligonucleotide is immobilized is preferably 10 μm to 5 cm in diameter. Problems may arise, if the size is smaller than the above, for example, detection becomes difficult, or if the size is larger than the above, the whole area occupied by arranged capture oligonucleotides is enlarged and hence handling property is degraded.

Upon immobilization of each capture oligonucleotide onto the substrate, each oligonucleotide may be immobilized as it is, but a linker may be added to an end of the oligonucleotide by increasing reactivity, and then the linker and the substrate or the carrier may be allow to react with each other. Examples of such a linker include an amino group or a homopolymer such as a homopolymer of thymidine residues.

Figure 2:
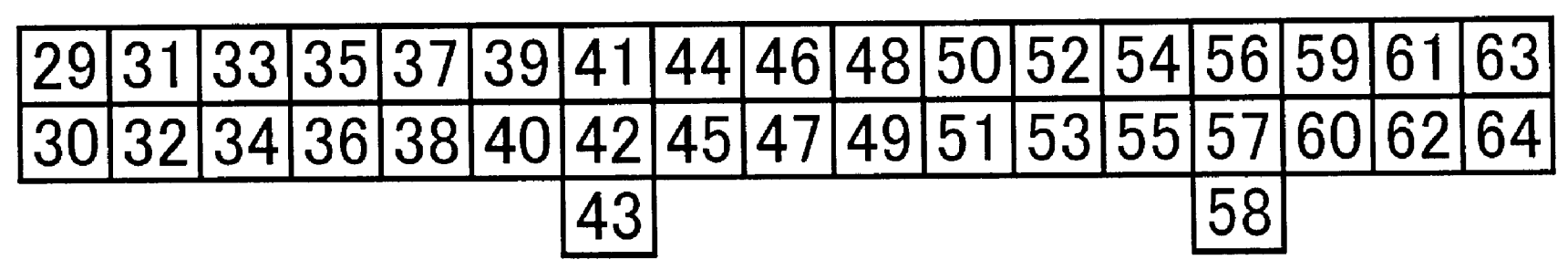

As for arrangement of the capture oligonucleotide on the substrate, to facilitate haplotype typing, capture oligonucleotides used to determine haplotypes are preferably arranged on the substrate by collectively disposing them in one section or arraying them in one line. More desirably, capture oligonucleotides with which polymorphisms are directly compared are arrayed vertically or horizontally. FIG. 2 shows an example of preferred arrangement of capture oligonucleotides immobilized on the substrate. In the figure, the squares represent positions at which each capture oligonucleotide is immobilized, the indicated numbers represent sequence numbers used in Sequence Listing, and each capture oligonucleotide has a corresponding nucleotide sequence.

One kind or two or more kinds of capture oligonucleotides may be immobilized on the substrate. Further, two or more kinds of capture oligonucleotides each having a common nucleotide sequence and a different chain length may be immobilized. If two or more kinds of oligonucleotides each having a different chain length are used as described above, stable results can be obtained even when experimental conditions differ. Further, two or more kinds of capture oligonucleotides each having a different corresponding polymorphic site may be immobilized. Furthermore, if a reference oligonucleotide, which contains a polymorphic site and has a nucleotide sequence complementary or homologous to a nucleotide sequence that does not exhibit a polymorphism and a length of 10 to 40 nucleotides, is further immobilized on the substrate, highly precise typing can be attained. The expression of "not exhibiting a polymorphism" used herein means that a nucleotide of a polymorphic site matches a corresponding nucleotide in the standard sequence of SEQ ID NO: 8.

A nucleic acid that is derived from specimen chum salmon and used for hybridization with an immobilized capture oligonucleotide (also referred to as "nucleic acid probe" hereinafter) is a nucleic acid including a mitochondrial DNA control region. The nucleic acid probe is not particularly limited so long as it does not inhibit hybridization, but DNA, RNA or the like is usually used. Further, a method for preparing the nucleic acid probe is not particularly limited so long as the method does not inhibit hybridization. Specifically, the nucleic acid probe can be prepared by extracting a nucleic acid from a cell or tissue of chum salmon and amplifying or isolating a sequence including the mitochondrial DNA control region by a method such as polymerase chain reaction (PCR), in vitro transcription or loop-mediated isothermal amplification. To prepare the nucleic acid, a method usually used in preparation of nucleic acids can be used. For example, there can be mentioned the method described in Zoological Science, 18, pp. 99–106.

The nucleic acid probe is prepared to contain at least one site of a polymorphism specific to each haplotype. Further, PCR primers used to prepare the nucleic acid probe are designed so as to have a nucleotide sequence complementary to a capture oligonucleotide except for a region of a sequence specific to each haplotype. The nucleic acid probe may be longer or shorter than a capture oligonucleotide so long as hybridization is possible. Further, to increase specificity in the PCR, initial preparation of the nucleic acid probe may be performed by using preliminary primers for preparing a region larger than a target nucleic acid probe, and then nucleic acid amplification may be performed by using secondary primers and the prepared nucleic acid as a template to obtain a nucleic acid probe. As such primers, there can be mentioned a combination of primers of SEQ ID NOS: 65 and 66 and a combination of primers of SEQ ID NOS: 67 and 68. Further, when specific nucleotide sequence regions used for the typing are remote from each other, nucleic acid probes corresponding to the respective specific regions can be prepared.

The nucleic acid probe is usually labeled in order to detect hybridization. A method for obtaining a labeled nucleic acid probe is not particularly limited so long as the method does not inhibit hybridization. Examples of such a method include a method of labeling a primer used to prepare a final nucleic acid probe beforehand, a method of labeling a nucleic acid probe during its preparation, a method of labeling a nucleic acid probe after its preparation and so forth.

As the method of labeling a primer beforehand, there can be mentioned a method of synthesizing a primer by using labeled nucleotides and so forth. As the method of labeling a nucleic acid probe during its preparation, there can be mentioned a method of incorporating a labeled nucleotide during preparation of the nucleic acid probe and so forth. Further, as the method of labeling a nucleic acid probe after its preparation, there can be mentioned a method of labeling by the method described in Japanese Patent Laid-Open Publication (Kokai) No. 10-287870 and so forth.

As a substance for labeling the nucleic acid probe, labeling substances used in usual hybridization methods can be used. Examples of such labeling substances include fluorescent substances, haptens and so forth. Specific examples of the fluorescent substances include fluorescein, rhodamine, phycoerythrin, Texas Red and cyanine type fluorescent dyes. Specific examples of the haptens include biotin, digoxigenin, dinitrophenyl and so forth.

The primers used to prepare a nucleic acid probe can be included in a haplotype typing kit together with a substrate on which capture oligonucleotides are immobilized.

Hybridization can be performed in the same manner as in usual hybridization of nucleic acids. Hereafter, specific methods will be exemplified.

A nucleic acid probe is added to a mixture composed of a salt solution such as standard saline citrate (SSC), a blocking solution such as sodium dodecylsulfate (SDS) and bovine serum albumin, and additives for accelerating a reaction. When the probe is double-stranded, denaturation is performed by heating or the like. Several microliters of a nucleic acid probe solution is added dropwise onto a substrate and heated for several hours (usually at 30–80° C.) to form hybrids from capture oligonucleotides immobilized on the substrate and the nucleic acid probe.

The substrate is immersed in an SSC solution or tetramethylammonium chloride solution of an appropriate concentration and heated (usually at 37–70° C.) so that only specific hybrids should be selectively retained on the substrate. At this time, SDS or the like may be added.

The hybrids are detected by using a fluorescent substance or a hapten that labels the nucleic acid probe. When the fluorescent substance is used, fluorescence labeling the hybridized nucleic acid probe is detected by using a fluorescence scanner for exclusive purpose.

When a hapten is used, a solution containing a conjugate (enzyme conjugate) of a protein that recognizes the hapten or a protein that binds thereto and alkaline phosphatase, horseradish peroxidase or the like is added onto the substrate and allowed to react at room temperature for several tens of minutes. Nonspecific adsorption of the enzyme conjugate to the substrate can be prevented by coating regions of the substrate with a protein such as casein or bovine serum albumin except for regions on which capture oligonucleotides are immobilized before the binding reaction of the hapten and the enzyme conjugate is performed. This treatment can be performed by, after oligonucleotides are immobilized, adding a solution of a protein such as casein to the substrate and leaving it at room temperature for several tens of minutes.

After the binding reaction of the enzyme conjugate and the hapten of the nucleic acid probe, the enzyme conjugate that does not bind to the hapten is washed off with an appropriate buffer containing a surfactant, and thus only the enzyme conjugate that binds to the hapten of the target nucleic acid remains on the substrate.

Then, only a portion where a hybrid is formed is visualized by adding a compound that develops color with an enzyme such as alkaline phosphatase or horseradish peroxidase bound to the enzyme conjugate and deposits at the site.

Examples of the compound used in this case include nitroblue tetrazolium chloride, 5-bromo-4-chloro-3-indolylphosphate-p-toluidine salt, 3,3',5,5'-tetramethylbenzidine and so forth.

Polymorphisms are detected by detecting deposited pigments or fluorescence at positions at which capture oligonucleotides are immobilized based on the obtained results of hybridization. Specifically, the color development level and fluorescence intensity of each capture oligonucleotide are compared, and those with a higher level is determined as hybridization positive. This detection is performed for each polymorphic site, and, when the polymorphic site matches any of haplotypes, the type is determined to be that type.

Upon determination, when one kind of capture oligonucleotide is used, the type is determined based on intensity of hybridization signal of the capture oligonucleotide. When two or more kinds of corresponding capture oligonucleotides having different lengths are used on the same site, the determination is performed by, for example, comparing the sum or the average value of all the hybridization signals of them, or the determination is performed based on a specific pattern of capture oligonucleotides of which hybridization signals can be obtained.

Hybridization signals and corresponding haplotypes obtained by using capture oligonucleotides having the nucleotide sequences of SEQ ID NOS: 29 to 64 are shown in Table 2.

Further, the kit of the present invention includes a substrate on which a capture oligonucleotide is immobilized. Further, the kit of the present invention can include primers for preparing a nucleic acid probe or labeled nucleic acid probe, buffer, reagents for hybridization such as enzyme conjugate that recognizes a hapten and so forth.

EXAMPLES

The present invention will be explained more specifically with reference to the following examples.

<1> Synthesis of Oligonucleotides

In a conventional manner, oligonucleotides were synthesized by using an oligonucleotide synthesizer (Perkin-Elmer Applied Biosystems), deprotected and dried. The dried oligonucleotides were dissolved in a buffer of 10 mM Tris-HCl (pH 7.5), 1 mM EDTA to prepare 100 pmol/μL oligonucleotide solutions. This synthesis method was used for the both of the capture oligonucleotides and oligonucleotides used as primers. The nucleotide sequences of the synthesized oligonucleotides are shown as SEQ ID NOS: 29 to 68. Of these, SEQ ID NOS: 29 to 64 are capture oligonucleotides, and SEQ ID NOS: 65 to 68 are primers. An amino group was added to the 5' end of each capture oligonucleotide by using the aforementioned synthesizer.

<2> Spotting of Capture Oligonucleotide onto Substrate

In an amount of 10 μL of each solution of oligonucleotide having an amino group at the 5' end was added with 10 μL of a microspotting solution (TeleChem International Inc.) and dividedly added onto a microtiter plate (Greiner Laboratory Inc.). Silanated slide glass (Matsunami Glass Ind. Ltd.) was disposed at a predetermined position of a spotting machine, and the spotting machine was operated. After the completion of spotting, the slide glass was applied with steam from hot water for several seconds and then irradiated with 30 mJ of ultraviolet ray. The slide glass was exposed to steam again for several seconds and then placed on a hot plate to remove moisture. The slide glass was rinsed with a 0.1% aqueous sodium dodecylsulfate solution and then with distilled water. The slide glass was immersed in a buffer of

TABLE 2

| Haplotype | SEQ ID NO | | | | | | | | | | | | | | | |
|---|---|---|---|---|---|---|---|---|---|---|---|---|---|---|---|---|
| 1 | 29 | 31 | 33 | 35 | 37 | 39 | 41 | 44 | 46 | 48 | 50 | 52 | 54 | 56 | 59 | 61 | 63 |
| 2 | 30 | 31 | 33 | 35 | 37 | 39 | 41 | 44 | 46 | 48 | 50 | 52 | 54 | 56 | 59 | 61 | 63 |
| 3 | 29 | 31 | 34 | 35 | 37 | 39 | 41 | 44 | 46 | 48 | 50 | 52 | 54 | 56 | 59 | 61 | 63 |
| 4 | 29 | 31 | 33 | 35 | 37 | 39 | 41 | 44 | 46 | 48 | 50 | 52 | 54 | 56 | 59 | 61 | 63 |
| 5 | 29 | 31 | 33 | 35 | 37 | 39 | 41 | 44 | 47 | 48 | 50 | 52 | 54 | 56 | 59 | 61 | 63 |
| 6 | 29 | 31 | 33 | 35 | 37 | 39 | 41 | 44 | 46 | 49 | 50 | 52 | 54 | 56 | 59 | 61 | 63 |
| 7 | 29 | 31 | 33 | 35 | 37 | 39 | 41 | 44 | 46 | 48 | 50 | 52 | 54 | 56 | 59 | 61 | 64 |
| 8 | 29 | 31 | 33 | 35 | 37 | 40 | 41 | 44 | 46 | 48 | 50 | 52 | 54 | 56 | 59 | 61 | 63 |
| 9 | 29 | 31 | 33 | 35 | 37 | 39 | 41 | 44 | 46 | 48 | 50 | 52 | 54 | 56 | 60 | 61 | 63 |
| 10 | 29 | 31 | 33 | 35 | 37 | 39 | 41 | 45 | 46 | 48 | 50 | 52 | 54 | 56 | 60 | 61 | 63 |
| 11 | 29 | 31 | 33 | 35 | 37 | 39 | 41 | 44 | 46 | 49 | 50 | 52 | 54 | 56 | 60 | 61 | 63 |
| 12 | 30 | 31 | 33 | 35 | 37 | 39 | 41 | 45 | 46 | 48 | 50 | 52 | 54 | 56 | 60 | 61 | 63 |
| 13 | 29 | 31 | 33 | 35 | 38 | 39 | 41 | 45 | 46 | 48 | 50 | 52 | 54 | 56 | 60 | 61 | 63 |
| 14 | 29 | 31 | 33 | 35 | 37 | 39 | 42 | 45 | 46 | 48 | 50 | 52 | 54 | 56 | 60 | 61 | 63 |
| 15 | 29 | 31 | 33 | 35 | 37 | 39 | 41 | 45 | 46 | 49 | 50 | 52 | 54 | 56 | 60 | 61 | 63 |
| 16 | 29 | 31 | 33 | 35 | 37 | 39 | 41 | 45 | 46 | 48 | 51 | 52 | 54 | 56 | 60 | 61 | 63 |
| 17 | 29 | 31 | 33 | 35 | 37 | 39 | 41 | 45 | 46 | 48 | 50 | 53 | 54 | 56 | 60 | 61 | 63 |
| 18 | 29 | 31 | 33 | 35 | 37 | 39 | 41 | 45 | 46 | 48 | 50 | 52 | 55 | 56 | 60 | 61 | 63 |
| 19 | 29 | 31 | 33 | 35 | 37 | 39 | 41 | 45 | 46 | 48 | 50 | 52 | 54 | 57 | 60 | 61 | 63 |
| 20 | 29 | 31 | 33 | 35 | 37 | 39 | 41 | 45 | 46 | 48 | 50 | 52 | 54 | 56 | 60 | 62 | 63 |
| 21 | 29 | 31 | 33 | 35 | 37 | 39 | 41 | 45 | 46 | 48 | 50 | 52 | 54 | 56 | 60 | 61 | 64 |
| 22 | 29 | 31 | 33 | 35 | 37 | 39 | 41 | 45 | 46 | 48 | 50 | 52 | 54 | 58 | 60 | 61 | 63 |
| 23 | 29 | 31 | 33 | 35 | 37 | 39 | 41 | 45 | 46 | 48 | 50 | 52 | 54 | 57 | 60 | 62 | 63 |
| 24 | 29 | 32 | 33 | 35 | 37 | 39 | 41 | 44 | 46 | 48 | 50 | 52 | 54 | 56 | 59 | 61 | 63 |
| 25 | 29 | 32 | 33 | 36 | 37 | 39 | 41 | 44 | 46 | 48 | 50 | 52 | 54 | 56 | 59 | 61 | 63 |
| 26 | 29 | 32 | 33 | 35 | 38 | 39 | 41 | 44 | 46 | 48 | 50 | 52 | 54 | 56 | 59 | 61 | 63 |
| 27 | 29 | 32 | 33 | 35 | 37 | 39 | 43 | 44 | 46 | 48 | 50 | 52 | 54 | 56 | 59 | 61 | 63 |
| 28 | 29 | 32 | 33 | 35 | 37 | 39 | 41 | 44 | 46 | 49 | 50 | 52 | 54 | 56 | 59 | 61 | 63 |

100 mM Tris-HCl (pH 7.5), 100 mM NaCl, 0.1% Triton X-100 containing 3% BSA (bovine serum albumin) at room temperature for 30 minutes for blocking. Then, the slide glass was dried at room temperature and washed with a buffer of 10 mM Tris-HCl (pH 7.5), 1 mM EDTA. The slide glass was dried at room temperature again and stored in a dry state in a dark cold place until use.

<3> Preparation of Probe Nucleic Acid

By using DNA of chum salmon as a template, a probe nucleic acid was prepared by PCR.

In an amount of 50 μL of blood obtained from chum salmon was placed in a microtube and washed with a physiological saline three times. This was added and mixed with 500 μl of a buffer of 10 mM Tris-HCl (pH 8.0), 0.1 M NaCl, 1 mM EDTA, 0.5% SDS and 500 μg/mL of proteinase K and incubated overnight at 37° C. The mixture was added with 500 μL of a solution of phenol, chloroform and isoamyl alcohol (25:24:1), stirred and then centrifuged at 12000 rpm for 1 minute to collect an aqueous phase. This operation was repeated three times. The obtained aqueous phase was added with 500 μL of a solution of chloroform and isoamyl alcohol (24:1), stirred and then centrifuged at 12000 rpm for 1 minute to collect an aqueous phase. This operation was repeated twice. DNA in the obtained aqueous phase was recovered by ethanol precipitation, dried and dissolved in TE buffer (10 mM Tris-HCl, 1 mM EDTA, pH 7.5) to obtain a PCR template solution.

As PCR primers, a combination of the primers of SEQ ID NOS: 65 and 66 and a combination of the primers of SEQ ID NO: 67 and 68 were used.

The composition of a PCR reaction mixture was 1 unit of Taq polymerase, 10 pmol each of the primers, 5 μl of a reaction buffer, 10 nmol each of dNTP, 0.5 μl of the template DNA solution and sterilized water in a total volume of 50 μl. The solution placed in a tube was set on a thermal cycler and heated at 94° C. for 3 minutes. Then, a reaction was performed with a cycle consisting of reactions at 94° C. for 45 seconds, at 58° C. for 45 seconds and at 72° C. for 1 minute, which was repeated 30 times, and then a reaction was allowed at 72° C. for 7 minutes.

In this example, electrophoresis using an agarose gel described below was performed as a verification test. However, it is unnecessary for diagnosis in practical clinical cases. In an amount of 1 μl of the PCR reaction mixture was taken and mixed with 1 μl of 6×migration pigment (30% glycerol, 0.25% bromophenol blue, 0.25% xylene cyanol) and 4 μl of distilled water. The mixture was migrated on a 2% agarose gel at 100 V for 90 minutes, and then the gel was immersed in distilled water containing 0.5 μg/ml ethidium bromide for 30 minutes and photographed by a CCD camera under irradiation of ultraviolet ray. As a result, it was confirmed that the desired amplified fragment was obtained.

<4> Hybridization

In an amount of 2 μl of the probe nucleic acid solution prepared in <3> was taken, added and mixed with 8 μl of ArrayIt Unihyb Hybridization Solution (TeleChem International Inc.), heated at 100° C. for 10 minutes and placed on ice for 5 minutes. In an amount of 5 μl of this probe nucleic acid solution was taken and placed on a substrate on which the capture oligonucleotides prepared in <2> were immobilized, and a cover glass was placed thereon. This was placed in a humid box, further placed in an incubator set at 35° C. and left standing for 120 minutes. The substrate was taken out and quickly immersed in a solution of 2×SSC, 0.1% SDS (2×SSC: 0.033 M NaCl, 0.033 M sodium citrate) at room temperature to remove the cover glass. Operations of immersing the substrate into the solution of 2×SSC, 0.1% SDS at room temperature for 5 minutes and immersing the substrate into a solution of 0.2×SSC, 0.1% SDS (0.2×SSC: 0.0033 M NaCl, 0.0033 M sodium citrate) at 43° C. were each repeated twice, and the substrate was finally immersed into 2×SSC.

<5> Detection of Fluorescence

After the hybridization, the substrate was taken out from 2×SSC, set in a centrifugal machine (Beckman) and centrifuged at 2000 rpm for 1 minute. Then, the substrate was set in Scan Array 4000 (GSI Lumonics) to detect fluorescence.

Figure 3:
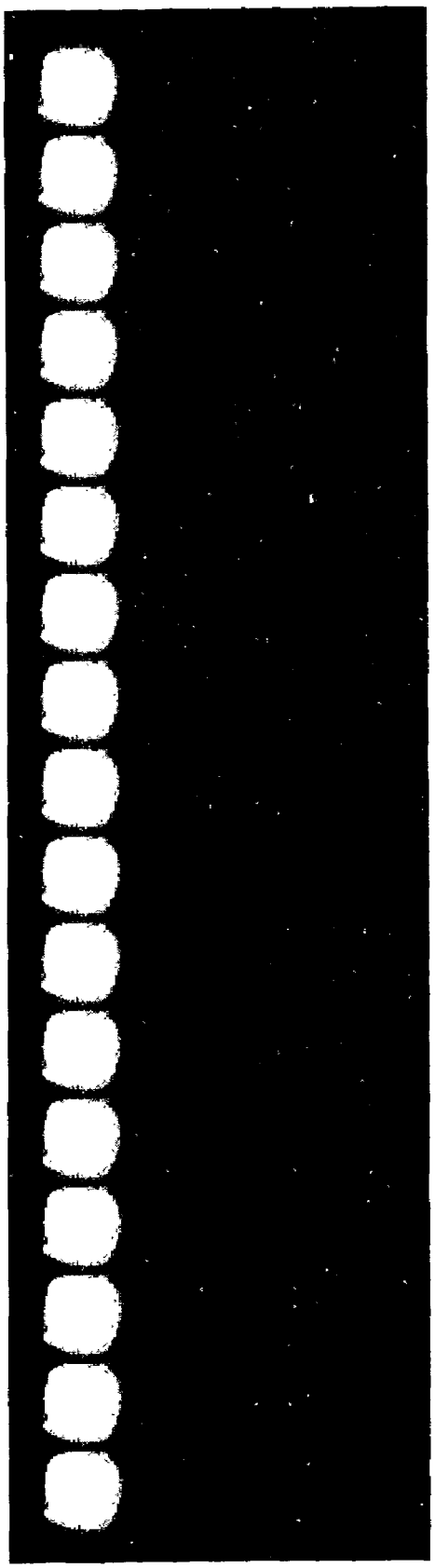
FIG. 3 shows results of hybridization performed by the method of the present invention.

The results of the above are shown in FIG. 3. Their relationships with the results of typing by the DNA sequencing method are shown in Table 3. It is evident that haplotype typing of chum salmon can be performed by the method of the present invention.

TABLE 3

| Haplotype (SEQ ID NO) | Correlation |
| --- | --- |
| 1 | ◯ |
| 2 | ◯ |
| 3 | ◯ |
| 4 | ◯ |
| 5 | ◯ |
| 6 | ◯ |
| 7 | ◯ |
| 8 | ◯ |
| 9 | ◯ |
| 10 | ◯ |
| 11 | ◯ |
| 12 | ◯ |
| 13 | ◯ |
| 14 | ◯ |
| 15 | ◯ |
| 16 | ◯ |
| 17 | ◯ |
| 18 | ◯ |
| 19 | ◯ |
| 20 | ◯ |
| 21 | ◯ |
| 22 | ◯ |
| 23 | ◯ |
| 24 | ◯ |
| 25 | ◯ |
| 26 | ◯ |
| 27 | ◯ |
| 28 | ◯ |

What is claimed is:

1. A kit for determining a haplotype of specimen chum salmon, which comprises an oligonucleotide-immobilized substrate obtained by immobilizing, on a substrate, one or more oligonucleotides that enable detection of a combination of polymorphisms selected from the group consisting of
   (2) 96D, T10C;
   (3) 96D, A42G;
   (4) 96D, A108C;
   (12) 96D, 386D, C395A, C154G, T10C;
   (13) 96D, 386D, C395A, C154G, T7OC;
   (14) 96D, 386D, C395A, C154G, A108C;
   (15) 96D, 386D, C395A, C154G, T231C;
   (16) 96D, 386D, C395A, C154G, C242T;
   (17) 96D, 386D, C395A, C154G, T250C;
   (18) 96D, 386D, C395A, C154G, A260G;
   (19) 96D, 386D, C395A, C154G, T339A;
   (20) 96D, 386D, C395A, C154G, T401C;
   (21) 96D, 386D, C395A, C154G, A471C;
   (22) 96D, 386D, C395A, C154G, T339A, C340T;
   (23) 96D, 386D, C395A, C154G, T339A, T401C; and
   (26) 96D, T30C, T70C,
   in a nucleotide sequence of mitochondrial DNA control region of chum salmon by hybridization, wherein the immobilized oligonucleotide comprises a position selected from the 10th, 30th, 42nd, 70th, 96th, 108th, 154th, 231st, 242nd, 250th, 260th, 339th, 340th, 386th, 395th, 401st and 471st positions of SEQ ID NO: 8, and determining the haplotype based on the combination of polymorphisms detected by hybridization of the oligonucleotides with a nucleic acid derived from the specimen chum salmon.

2. The kit according to claim 1, wherein each oligonucleotide has a nucleotide sequence complementary or homologous to a nucleotide sequence of a region including a polymorphic site and has a length of 10 to 40 nucleotides.

3. The kit according to claim 1, further comprising a reference oligonucleotide immobilized on the substrate, which comprises the polymorphic site and has a nucleotide sequence complementary or homologous to a nucleotide sequence that does not exhibit a polymorphism and a length of 10 to 40 nucleotides.

4. The kit according to claim 1, wherein the one or more oligonucleotides are immobilized on the substrate, which surface is coated with carbodiimide groups or isocyanate groups, through a reaction between a carbodiimide group or isocyanate group and a linker added to an end of the one or more oligonucleotides.

5. The kit according to claim 4, wherein the linker is an amino group or a compound that has an amino group or a homopolymer of thymidine residues at an end thereof.

6. The kit according to claim 4, wherein the one or more oligonucleotides are immobilized on a site having a size of 10 μm to 5 cm in diameter of the surface of the substrate.

7. The kit according to claim 1, wherein the one or more oligonucleotides are DNA, RNA, peptide nucleic acid or locked nucleic acid.

8. The kit according to claim 1, wherein at least one of the oligonucleotides is an oligonucleotide of which binding affinity in hybridization is reduced by substitution of a spacer compound for an arbitrary nucleotide unrelated to a gene polymorphism.

9. The kit according to claim 8, wherein the spacer compound is a nucleic acid structure that does not have complementary binding property to any kind of nucleotides.

10. The kit according to claim 1, wherein a homing area of the specimen chum salmon is estimated based on the determined haplotype of the specimen chum salmon.

11. The kit according to claim 1, wherein each oligonucleotide is selected from the nucleotide sequences of SEQ ID NOS: 29 to 64 or oligonucleotides having a nucleotide sequence obtained by extending or shortening any of these nucleotide sequences on the 5' or 3' side or the both sides.

12. A method for determining a haplotype of specimen chum salmon which comprises hybridizing a nucleic acid derived from the specimen chum salmon with each oligonucleotide contained in the kit according to any one of claims 1 and 2–11, detecting presence or absence of formation of a hybrid of each oligonucleotide and the nucleic acid derived from the specimen chum salmon and identifying a polymorphism in the nucleotide sequence of the chum salmon mitochondrial DNA control region to determine the haplotype of the specimen.

13. A kit for determining a haplotype of specimen chum salmon, which comprises an oligonucleotide-immobilized substrate obtained by immobilizing, on a substrate, one or more oligonucleotides that enable detection of a polymorphism or combination of polymorphisms in a nucleotide sequence of mitochondrial DNA control region of chum salmon by hybridization, wherein the polymorphism or combination of polymorphisms is selected from the group consisting of T10C, A42G, T70C, A108C, C242T, T250C, A260G, T339A, C340T and T401C of SEQ ID NO: 8, and determining the haplotype based on the polymorphism or combination of polymorphisms detected by hybridization of the oligonucleotides with a nucleic acid derived from the specimen chum salmon.

* * * * *

UNITED STATES PATENT AND TRADEMARK OFFICE
CERTIFICATE OF CORRECTION

| | | |
|---|---|---|
| PATENT NO. | : 7,105,299 B2 | Page 1 of 1 |
| APPLICATION NO. | : 10/317449 | |
| DATED | : September 12, 2006 | |
| INVENTOR(S) | : Moriya et al. | |

It is certified that error appears in the above-identified patent and that said Letters Patent is hereby corrected as shown below:

Title page, (56) References Cited, U.S. PATENT DOCUMENTS, --5,780,233 07/1998

Guo, et al.-- should be added

Title page, (56) References Cited, OTHER PUBLICATIONS, Column 2, Line 1,

"Levels of Intraspeciolic" should be changed to --Levels of Intraspecific--

Column 45, Line 11, "T7OC;" should be changed to --T70C;--

Signed and Sealed this

Fifteenth Day of May, 2007

JON W. DUDAS
*Director of the United States Patent and Trademark Office*

SEQUENCE LISTING

<160> NUMBER OF SEQ ID NOS: 68

<210> SEQ ID NO 1
<211> LENGTH: 481
<212> TYPE: DNA
<213> ORGANISM: Oncorhynchus keta

<400> SEQUENCE: 1

```
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aacccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                    481
```

<210> SEQ ID NO 2
<211> LENGTH: 481
<212> TYPE: DNA
<213> ORGANISM: Oncorhynchus keta

<400> SEQUENCE: 2

```
gcggctacac cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aacccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                    481
```

<210> SEQ ID NO 3
<211> LENGTH: 481
<212> TYPE: DNA
<213> ORGANISM: Oncorhynchus keta

<400> SEQUENCE: 3

```
gcggctacat cccgcacatt tgtaaatgct ataacttgta agcccaatgt tatactacac      60
tatgtataat attacatatt atgtatttac ccatatataa tactgcacgt gagtagtaca     120
ttatatgtat tatcaacata tacttatttt aacccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
```

```
a                                                                          481

<210> SEQ ID NO 4
<211> LENGTH: 481
<212> TYPE: DNA
<213> ORGANISM: Oncorhynchus keta

<400> SEQUENCE: 4
gcggctacat cccgcacatt tgtaaatgct ataacttgta aacccaatgt tatactacac      60
tatgtataat attacatatt atgtatttac ccatatataa tactgcccgt gagtagtaca     120
ttatatgtat tatcaacata tacttatttt aaccccctcat acatcagcac taatccaagg    180
tttacattaa gcaaaacacg tgataataac caactaagtt gtctgcaact gattaattgc     240
cgcatcaata aacctccaac taacacgggc tccgtcttta cccaccaact ttcagcatca     300
gtcctgctta atgtagtaag aaccgaccaa cgatatatca gtaggcatac tcttaatgat     360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                       481

<210> SEQ ID NO 5
<211> LENGTH: 481
<212> TYPE: DNA
<213> ORGANISM: Oncorhynchus keta

<400> SEQUENCE: 5
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aaccccctcat acatcagcac taatccaagg    180
tttacattaa gctaaacacg tgataataac caactaagtt gtctgcaact gattaattgc     240
cgcatcaata aacctccaac taacacgggc tccgtcttta cccaccaact ttcagcatca     300
gtcctgctta atgtagtaag aaccgaccaa cgatatatca gtaggcatac tcttaatgat     360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                       481

<210> SEQ ID NO 6
<211> LENGTH: 481
<212> TYPE: DNA
<213> ORGANISM: Oncorhynchus keta

<400> SEQUENCE: 6
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aaccccctcat acatcagcac taatccaagg    180
tttacattaa gcaaaacacg tgataataac caactaagtt gtctgcaacc gattaattgc     240
cgcatcaata aacctccaac taacacgggc tccgtcttta cccaccaact ttcagcatca     300
gtcctgctta atgtagtaag aaccgaccaa cgatatatca gtaggcatac tcttaatgat     360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
```

```
a                                                                         481

<210> SEQ ID NO 7
<211> LENGTH: 481
<212> TYPE: DNA
<213> ORGANISM: Oncorhynchus keta

<400> SEQUENCE: 7
gcggctacat cccgcacatt tgtaaatgct ataacttgta aacccaatgt tatactacac    60
tatgtataat attacatatt atgtatttac ccatatataa tactgcacgt gagtagtaca   120
ttatatgtat tatcaacata tacttatttt aacccctcat acatcagcac taatccaagg   180
tttacattaa gcaaaacacg tgataataac caactaagtt gtctgcaact gattaattgc   240
cgcatcaata aacctccaac taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttaggtcgca tctcgtgaat tattcctggc atttggttcc   420
taagtcaagg gctatcctta agaaaccacc ccctgaaagc cgaatgtaac gcatctggtt   480
a                                                                    481

<210> SEQ ID NO 8
<211> LENGTH: 482
<212> TYPE: DNA
<213> ORGANISM: Oncorhynchus keta

<400> SEQUENCE: 8
gcggctacat cccgcacatt tgtaaatgct ataacttgta aacccaatgt tatactacac    60
tatgtataat attacatatt atgtatttac ccataatata tactgcacg tgagtagtac    120 attatatgta ttatcaacat atacttattt taacccctca tacatcagca ctaatccaag   180
gtttacatta agcaaaacac gtgataataa ccaactaagt tgtctgcaac tgattaattg   240
ccgcatcaat aaacctccaa ctaacacggg ctccgtcttt acccaccaac tttcagcatc   300
agtcctgctt aatgtagtaa gaaccgacca acgatatatc agtaggcata ctcttaatga   360
tggtcaggga cagaaatcgt attaggtcgc atctcgtgaa ttattcctgg catttggttc   420
ctaagtcaag ggctatccct taagaaaccac ccctgaaag ccgaatgtaa agcatctggt   480
ta                                                                   482

<210> SEQ ID NO 9
<211> LENGTH: 480
<212> TYPE: DNA
<213> ORGANISM: Oncorhynchus keta

<400> SEQUENCE: 9
gcggctacat cccgcacatt tgtaaatgct ataacttgta aacccaatgt tatactacac    60
tatgtataat attacatatt atgtatttac ccatatataa tactgcacgt gagtagtaca   120
ttatatgtat tatcaacata tacttatttt aacccctcat acatcagcac taatccaagg   180
tttacattaa gcaaaacacg tgataataac caactaagtt gtctgcaact gattaattgc   240
cgcatcaata aacctccaac taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttagtcgcat ctagtgaatt attcctggca tttggttcct   420
aagtcaaggg ctatccttaa gaaaccaccc cctgaaagcc gaatgtaaag catctggtta   480
```

<210> SEQ ID NO 10
<211> LENGTH: 480
<212> TYPE: DNA
<213> ORGANISM: Oncorhynchus keta

<400> SEQUENCE: 10

```
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aagccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttagtcgcat ctagtgaatt attcctggca tttggttcct    420
aagtcaaggg ctatccttaa gaaaccaccc cctgaaagcc gaatgtaaag catctggtta    480
```

<210> SEQ ID NO 11
<211> LENGTH: 480
<212> TYPE: DNA
<213> ORGANISM: Oncorhynchus keta

<400> SEQUENCE: 11

```
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aaccctcat acatcagcac taatccaagg    180
tttacattaa gcaaaacacg tgataataac caactaagtt gtctgcaacc gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttagtcgcat ctagtgaatt attcctggca tttggttcct    420
aagtcaaggg ctatccttaa gaaaccaccc cctgaaagcc gaatgtaaag catctggtta    480
```

<210> SEQ ID NO 12
<211> LENGTH: 480
<212> TYPE: DNA
<213> ORGANISM: Oncorhynchus keta

<400> SEQUENCE: 12

```
gcggctacac cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aagccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttagtcgcat ctagtgaatt attcctggca tttggttcct    420
aagtcaaggg ctatccttaa gaaaccaccc cctgaaagcc gaatgtaaag catctggtta    480
```

<210> SEQ ID NO 13
<211> LENGTH: 480
<212> TYPE: DNA
<213> ORGANISM: Oncorhynchus keta

<400> SEQUENCE: 13

```
gcggctacat cccgcacatt tgtaaatgct ataacttgta aacccaatgt tatactacac      60
tatgtataac attacatatt atgtatttac ccatatataa tactgcacgt gagtagtaca     120
ttatatgtat tatcaacata tacttatttt aagccctcat acatcagcac taatccaagg     180
tttacattaa gcaaaacacg tgataataac caactaagtt gtctgcaact gattaattgc     240
cgcatcaata aacctccaac taacacgggc tccgtcttta cccaccaact ttcagcatca     300
gtcctgctta atgtagtaag aaccgaccaa cgatatatca gtaggcatac tcttaatgat     360
ggtcagggac agaaatcgta ttagtcgcat ctagtgaatt attcctggca tttggttcct     420
aagtcaaggg ctatccttaa gaaaccaccc cctgaaagcc gaatgtaaag catctggtta     480
```

<210> SEQ ID NO 14
<211> LENGTH: 480
<212> TYPE: DNA
<213> ORGANISM: Oncorhynchus keta

<400> SEQUENCE: 14

```
gcggctacat cccgcacatt tgtaaatgct ataacttgta aacccaatgt tatactacac      60
tatgtataat attacatatt atgtatttac ccatatataa tactgcccgt gagtagtaca     120
ttatatgtat tatcaacata tacttatttt aagccctcat acatcagcac taatccaagg     180
tttacattaa gcaaaacacg tgataataac caactaagtt gtctgcaact gattaattgc     240
cgcatcaata aacctccaac taacacgggc tccgtcttta cccaccaact ttcagcatca     300
gtcctgctta atgtagtaag aaccgaccaa cgatatatca gtaggcatac tcttaatgat     360
ggtcagggac agaaatcgta ttagtcgcat ctagtgaatt attcctggca tttggttcct     420
aagtcaaggg ctatccttaa gaaaccaccc cctgaaagcc gaatgtaaag catctggtta     480
```

<210> SEQ ID NO 15
<211> LENGTH: 480
<212> TYPE: DNA
<213> ORGANISM: Oncorhynchus keta

<400> SEQUENCE: 15

```
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aagccctcat acatcagcac taatccaagg     180
tttacattaa gcaaaacacg tgataataac caactaagtt gtctgcaacc gattaattgc     240
cgcatcaata aacctccaac taacacgggc tccgtcttta cccaccaact ttcagcatca     300
gtcctgctta atgtagtaag aaccgaccaa cgatatatca gtaggcatac tcttaatgat     360
ggtcagggac agaaatcgta ttagtcgcat ctagtgaatt attcctggca tttggttcct     420
aagtcaaggg ctatccttaa gaaaccaccc cctgaaagcc gaatgtaaag catctggtta     480
```

<210> SEQ ID NO 16
<211> LENGTH: 480
<212> TYPE: DNA
<213> ORGANISM: Oncorhynchus keta

<400> SEQUENCE: 16

```
gcggctacat cccgcacatt tgtaaatgct ataacttgta aacccaatgt tatactacac      60
tatgtataat attacatatt atgtatttac ccatatataa tactgcacgt gagtagtaca     120
ttatatgtat tatcaacata tacttatttt aagccctcat acatcagcac taatccaagg     180
tttacattaa gcaaaacacg tgataataac caactaagtt gtctgcaact gattaattgc     240
```
tgcatcaata aacctccaac taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttagtcgcat ctagtgaatt attcctggca tttggttcct   420
aagtcaaggg ctatccttaa gaaaccaccc cctgaaagcc gaatgtaaag catctggtta   480

<210> SEQ ID NO 17
<211> LENGTH: 480
<212> TYPE: DNA
<213> ORGANISM: Oncorhynchus keta

<400> SEQUENCE: 17
gcggctacat cccgcacatt tgtaaatgct ataacttgta aacccaatgt tatactacac    60
tatgtataat attacatatt atgtatttac ccatatataa tactgcacgt gagtagtaca   120
ttatatgtat tatcaacata tacttatttt aagccctcat acatcagcac taatccaagg   180
tttacattaa gcaaaacacg tgataataac caactaagtt gtctgcaact gattaattgc   240
cgcatcaaca aacctccaac taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttagtcgcat ctagtgaatt attcctggca tttggttcct   420
aagtcaaggg ctatccttaa gaaaccaccc cctgaaagcc gaatgtaaag catctggtta   480

<210> SEQ ID NO 18
<211> LENGTH: 480
<212> TYPE: DNA
<213> ORGANISM: Oncorhynchus keta

<400> SEQUENCE: 18
gcggctacat cccgcacatt tgtaaatgct ataacttgta aacccaatgt tatactacac    60
tatgtataat attacatatt atgtatttac ccatatataa tactgcacgt gagtagtaca   120
ttatatgtat tatcaacata tacttatttt aagccctcat acatcagcac taatccaagg   180
tttacattaa gcaaaacacg tgataataac caactaagtt gtctgcaact gattaattgc   240
cgcatcaata aacctccagc taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttagtcgcat ctagtgaatt attcctggca tttggttcct   420
aagtcaaggg ctatccttaa gaaaccaccc cctgaaagcc gaatgtaaag catctggtta   480

<210> SEQ ID NO 19
<211> LENGTH: 480
<212> TYPE: DNA
<213> ORGANISM: Oncorhynchus keta

<400> SEQUENCE: 19
gcggctacat cccgcacatt tgtaaatgct ataacttgta aacccaatgt tatactacac    60
tatgtataat attacatatt atgtatttac ccatatataa tactgcacgt gagtagtaca   120
ttatatgtat tatcaacata tacttatttt aagccctcat acatcagcac taatccaagg   180
tttacattaa gcaaaacacg tgataataac caactaagtt gtctgcaact gattaattgc   240
cgcatcaata aacctccaac taacacgggc tccgtcttta cccaccaact ttcagcatca   300
gtcctgctta atgtagtaag aaccgaccaa cgatataaca gtaggcatac tcttaatgat   360
ggtcagggac agaaatcgta ttagtcgcat ctagtgaatt attcctggca tttggttcct   420

```
aagtcaaggg ctatccttaa gaaaccaccc cctgaaagcc gaatgtaaag catctggtta    480

<210> SEQ ID NO 20
<211> LENGTH: 480
<212> TYPE: DNA
<213> ORGANISM: Oncorhynchus keta

<400> SEQUENCE: 20
gcggctacat cccgcacatt tgtaaatgct ataacttgta aacccaatgt tatactacac     60
tatgtataat attacatatt atgtatttac ccatatataa tactgcacgt gagtagtaca    120
ttatatgtat tatcaacata tacttatttt aagccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttagtcgcat ctagtgaact attcctggca tttggttcct    420
aagtcaaggg ctatccttaa gaaaccaccc cctgaaagcc gaatgtaaag catctggtta    480

<210> SEQ ID NO 21
<211> LENGTH: 480
<212> TYPE: DNA
<213> ORGANISM: Oncorhynchus keta

<400> SEQUENCE: 21
gcggctacat cccgcacatt tgtaaatgct ataacttgta aacccaatgt tatactacac     60
tatgtataat attacatatt atgtatttac ccatatataa tactgcacgt gagtagtaca    120
ttatatgtat tatcaacata tacttatttt aagccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttagtcgcat ctagtgaatt attcctggca tttggttcct    420
aagtcaaggg ctatccttaa gaaaccaccc cctgaaagcc gaatgtaacg catctggtta    480

<210> SEQ ID NO 22
<211> LENGTH: 480
<212> TYPE: DNA
<213> ORGANISM: Oncorhynchus keta

<400> SEQUENCE: 22
gcggctacat cccgcacatt tgtaaatgct ataacttgta aacccaatgt tatactacac     60
tatgtataat attacatatt atgtatttac ccatatataa tactgcacgt gagtagtaca    120
ttatatgtat tatcaacata tacttatttt aagccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatataata gtaggcatac tcttaatgat    360
ggtcagggac agaaatcgta ttagtcgcat ctagtgaatt attcctggca tttggttcct    420
aagtcaaggg ctatccttaa gaaaccaccc cctgaaagcc gaatgtaaag catctggtta    480

<210> SEQ ID NO 23
<211> LENGTH: 480
<212> TYPE: DNA
<213> ORGANISM: Oncorhynchus keta
```

<400> SEQUENCE: 23

```
gcggctacat cccgcacatt tgtaaatgct ataacttgta aacccaatgt tatactacac    60
tatgtataat attacatatt atgtatttac ccatatataa tactgcacgt gagtagtaca   120
ttatatgtat tatcaacata tacttatttt aagccctcat acatcagcac taatccaagg   180
tttacattaa gcaaaacacg tgataataac caactaagtt gtctgcaact gattaattgc   240
cgcatcaata aacctccaac taacacgggc tccgtcttta cccaccaact ttcagcatca   300
gtcctgctta atgtagtaag aaccgaccaa cgatataaca gtaggcatac tcttaatgat   360
ggtcagggac agaaatcgta ttagtcgcat ctagtgaact attcctggca tttggttcct   420
aagtcaaggg ctatccttaa gaaaccaccc cctgaaagcc gaatgtaaag catctggtta   480
```

<210> SEQ ID NO 24
<211> LENGTH: 481
<212> TYPE: DNA
<213> ORGANISM: Oncorhynchus keta

<400> SEQUENCE: 24

```
gcggctacat cccgcacatt tgtaaatgcc ataacttgta aacccaatgt tatactacac    60
tatgtataat attacatatt atgtatttac ccatatataa tactgcacgt gagtagtaca   120
ttatatgtat tatcaacata tacttatttt aaccctcat acatcagcac taatccaagg   180
tttacattaa gcaaaacacg tgataataac caactaagtt gtctgcaact gattaattgc   240
cgcatcaata aacctccaac taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttaggtcgca tctcgtgaat tattcctggc atttggttcc   420
taagtcaagg gctatcctta agaaaccacc ccctgaaagc cgaatgtaaa gcatctggtt   480
a                                                                   481
```

<210> SEQ ID NO 25
<211> LENGTH: 481
<212> TYPE: DNA
<213> ORGANISM: Oncorhynchus keta

<400> SEQUENCE: 25

```
gcggctacat cccgcacatt tgtaaatgcc ataacttgta aacccaatgt tatacttcac    60
tatgtataat attacatatt atgtatttac ccatatataa tactgcacgt gagtagtaca   120
ttatatgtat tatcaacata tacttatttt aaccctcat acatcagcac taatccaagg   180
tttacattaa gcaaaacacg tgataataac caactaagtt gtctgcaact gattaattgc   240
cgcatcaata aacctccaac taacacgggc tccgtcttta cccaccaact ttcagcatca   300
gtcctgctta atgtagtaag aaccgaccaa cgatatatca gtaggcatac tcttaatgat   360
ggtcagggac agaaatcgta ttaggtcgca tctcgtgaat tattcctggc atttggttcc   420
taagtcaagg gctatcctta agaaaccacc ccctgaaagc cgaatgtaaa gcatctggtt   480
a                                                                   481
```

<210> SEQ ID NO 26
<211> LENGTH: 481
<212> TYPE: DNA
<213> ORGANISM: Oncorhynchus keta

<400> SEQUENCE: 26

```
gcggctacat cccgcacatt tgtaaatgcc ataacttgta aacccaatgt tatactacac      60
tatgtataac attacatatt atgtatttac ccatatataa tactgcacgt gagtagtaca     120
ttatatgtat tatcaacata tacttatttt aaccccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                    481
```

<210> SEQ ID NO 27
<211> LENGTH: 481
<212> TYPE: DNA
<213> ORGANISM: Oncorhynchus keta

<400> SEQUENCE: 27

```
gcggctacat cccgcacatt tgtaaatgcc ataacttgta aacccaatgt tatactacac      60
tatgtataat attacatatt atgtatttac ccatatataa tactgctcgt gagtagtaca     120
ttatatgtat tatcaacata tacttatttt aaccccctcat acatcagcac taatccaagg    180
tttacattaa gcaaaacacg tgataataac caactaagtt gtctgcaact gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                    481
```

<210> SEQ ID NO 28
<211> LENGTH: 481
<212> TYPE: DNA
<213> ORGANISM: Oncorhynchus keta

<400> SEQUENCE: 28

```
gcggctacat cccgcacatt tgtaaatgcc ataacttgta aacccaatgt tatactacac      60
tatgtataat attacatatt atgtatttac ccatatataa tactgcacgt gagtagtaca     120
ttatatgtat tatcaacata tacttatttt aaccccctcat acatcagcac taatccaagg    180
tttacattaa gcaaaacacg tgataataac caactaagtt gtctgcaacc gattaattgc    240
cgcatcaata aacctccaac taacacgggc tccgtcttta cccaccaact ttcagcatca    300
gtcctgctta atgtagtaag aaccgaccaa cgatatatca gtaggcatac tcttaatgat    360
ggtcagggac agaaatcgta ttaggtcgca tctcgtgaat tattcctggc atttggttcc    420
taagtcaagg gctatcctta agaaaccacc ccctgaaagc cgaatgtaaa gcatctggtt    480
a                                                                    481
```

<210> SEQ ID NO 29
<211> LENGTH: 20
<212> TYPE: DNA
<213> ORGANISM: Oncorhynchus keta

<400> SEQUENCE: 29

```
gcggctacat cccgcacatt                                                 20
```

```
<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 30
gcggctacac cccgcacatt                                                    20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 31
tgtaaatgct ataacttgta                                                    20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 32
tgtaaatgcc ataacttgta                                                    20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence:capture

<400> SEQUENCE: 33
aacttgtaaa cccaatgtt                                                     19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence:capture

<400> SEQUENCE: 34
aacttgtaag cccaatgtt                                                     19

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 35
tgttatacta cactatgtat                                                    20

<210> SEQ ID NO 36
<211> LENGTH: 20
<212> TYPE: DNA
<213> ORGANISM: Artificial Sequence
<220> FEATURE:
```

<223> OTHER INFORMATION: Description of Artificial Sequence:capture

<400> SEQUENCE: 36
tgttatactt cactatgtat                                           20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 37
tatgtataat attacatatt                                           20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 38
tatgtataac attacatatt                                           20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:capture

<400> SEQUENCE: 39
ttacccatat ataatactg                                            19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 40
ttacccataa tataatactg                                           20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 41
taatactgca cgtgagtagt                                           20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 42
taatactgcc cgtgagtagt                                           20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 43
taatactgct cgtgagtagt                                                  20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 44
cttattttaa cccctcatac                                                  20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 45
cttattttaa gccctcatac                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 46
tacattaagc aaaacacgtg                                                  20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 47
tacattaagc taaacacgtg                                                  20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 48
gtctgcaact gattaattgc                                                  20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:capture

```
<400> SEQUENCE: 49
gtctgcaacc gattaattgc                                              20

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:capture

<400> SEQUENCE: 50
gattaattgc cgcatcaa                                                18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:capture

<400> SEQUENCE: 51
gattaattgc tgcatcaa                                                18

<210> SEQ ID NO 52
<211> LENGTH: 17
<212> TYPE: DNA
<213> ORGANISM: Artificial Sequence
<220> FEATURE:
<223> OTHER INFORMATION: Description of Artificial Sequence:capture

<400> SEQUENCE: 52
gcatcaataa acctcca                                                 17

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence:capture

<400> SEQUENCE: 53
gcatcaacaa acctcca                                                 17

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 54
aaacctccaa ctaacacggg                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 55
aaacctccag ctaacacggg                                              20

<210> SEQ ID NO 56
<211> LENGTH: 20
```

```
<212> TYPE: DNA
<213> ORGANISM: Artificial Sequence
<220> FEATURE:
<223> OTHER INFORMATION: Description of Artificial Sequence:capture

<400> SEQUENCE: 56
acgatatatc agtaggcata                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 57
acgatataac agtaggcata                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 58
acgatataat agtaggcata                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 59
gtattaggtc gcatctcgtg                                              20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence:capture

<400> SEQUENCE: 60
gtattagtcg catctagtg                                               19

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 61
gtgaattatt cctggcattt                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 62
```

```
gtgaactatt cctggcattt                                               20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 63
gaatgtaaag catctggtta                                               20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:capture

<400> SEQUENCE: 64
gaatgtaacg catctggtta                                               20

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 65
aactactctc tggcggct                                                 18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 66
ttggtgggta aagacgga                                                 18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 67
agtcctgctt aatgtagt                                                 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 68
ataagattga caccatta                                                 18
```